United States Patent [19]

Itoh

[11] Patent Number: 4,578,802

[45] Date of Patent: Mar. 25, 1986

[54] X-RAY DIAGNOSTIC APPARATUS FOR ALLOWING STEREOSCOPIC VISUALIZATION ON X-RAY IMAGES OF AN OBJECT UNDER EXAMINATION

[75] Inventor: Katsutoshi Itoh, Tochigi, Japan

[73] Assignee: Kabushiki Kaisha Toshiba, Japan

[21] Appl. No.: 623,506

[22] Filed: Jun. 22, 1984

[30] Foreign Application Priority Data

Jun. 27, 1983 [JP] Japan ................. 58-115388

[51] Int. Cl.⁴ .............................. A61B 6/02
[52] U.S. Cl. ..................... 378/41; 378/99
[58] Field of Search ............... 358/111; 378/41, 42, 378/99, 100

[56] References Cited

U.S. PATENT DOCUMENTS

| | | | |
|---|---|---|---|
| 3,076,054 | 1/1963 | Simon | 378/99 |
| 3,309,519 | 3/1967 | Euler et al. | 378/41 |
| 3,585,382 | 6/1971 | Suganuma | 378/99 |
| 3,783,282 | 1/1974 | Hoppenstein | 378/41 |
| 4,075,492 | 2/1978 | Boyd et al. | 250/385 |

FOREIGN PATENT DOCUMENTS

041749 12/1981 European Pat. Off. .
041752 12/1981 European Pat. Off. .
57-52284 3/1982 Japan .

OTHER PUBLICATIONS

Patent Abstracts of Japan, unexamined applications, E section, vol. 7, No. 208, Sep. 14, 1983.
Sklebitz, et al., "Tomoskopie: Schichten Ohne Mechanische Bewegung," Scientific Exhibition SE H14, XVth International Congress of Radiology, Jun. 24, 1981.

*Primary Examiner*—Carolyn E. Fields
*Attorney, Agent, or Firm*—Finnegan, Henderson, Farabow, Garrett & Dunner

[57] ABSTRACT

An X-ray diagnostic apparatus for allowing stereoscopic visualization on X-ray images of an object under examination includes at least a stereoscopic X-ray tube, a deflection coil type X-ray image intensifier, and a single television camera. The right-viewed and left-viewed X-ray visual images are alternately output from the image intensifier with a given deviation between centers of those images. Those visual images are alternately incident upon the respective image conversion regions of the TV camera, whereby the electrical scanning is also done alternately for each of the image conversion regions so as to prevent the after-image effect.

11 Claims, 9 Drawing Figures

X-RAY DIAGNOSTIC APPARATUS FOR ALLOWING STEREOSCOPIC VISUALIZATION ON X-RAY IMAGES OF AN OBJECT UNDER EXAMINATION

BACKGROUND OF THE INVENTION

1. Field of the Invention

The present invention relates to an X-ray diagnostic apparatus for allowing stereoscopic visualization of X-ray images, e.g., angiograms of an object under examination.

2. Description of the Prior Art

In a conventional X-ray diagnostic apparatus set forth in the preamble, there are usually provided two X-ray tubes, or a single X-ray tube having two X-ray radiation sources. An object under examination, e.g., a patient is radiated by the X-rays by alternately energizing those two X-ray tubes or two radiation sources. Those X-rays penetrate through the object and are incident upon a visual image converter such as an X-ray image intensifier. The image converter converts the X-ray transmission images into visual X-ray images. Those visual X-ray images are received by an image senser, e.g., a television camera to be converted into X-ray image signals. The X-ray image signals are electrically processed in a digital subtraction circuit so as to obtain angiographic images of the object.

To realize better stereoscopic visualization of the angiographic images, the image senser for receiving the X-ray transmission images must prevent an influence of the after-image phenomenon from the successive image conversion. That is, for example when the single image senser receives the succeeding transmission X-ray image before the after-image phenomenon of the preceeding transmission X-ray image still remains in the image senser, those transmission X-ray images are mixed up therein, so that the stereoscopic visualization is extremely deteriorated.

When a vidicon is employed as the pick-up tube of the above image senser, it practically requires at least 50 millisecond-time interval to avoid the influence of the after-image thereof. Accordingly, if a single vidicon TV camera is used, the time interval between the successive X-ray projections from the right and left X-ray sources need more than 50 milliseconds in order to prevent deterioration of the stereoscopic visualization by the vidicon that is caused by unnecessarily mixing the incident X-ray image with the previously stored image.

If time intervals of the X-ray projection become more than 50 milliseconds, the visual images of the object which have taken at two different projection angles have different shapes, or contours from each other in case that the shape of the object changes at a rapid speed, e.g., coronary arteries. Accordingly, it may cause quality of the stereoscopic visualization to be deteriorated.

In principle, such stereoscopic visualization can be achieved by observing simultaneously an object at two different angles of observation, or with a given parallax. The time intervals of the X-ray projection must be therefore chosen short as permitted as possible, because it is impossible to simultaneously project X-rays toward the object from two X-ray sources in the normal stereoscopic X-ray diagnostic apparatus. It is necessary to shorter the X-ray projection interval in order to achieve the stereoscopic visualization for the smooth movement of the moving portion of the object at a high speed.

Furthermore, the right view and the left view for the object under examination are optically and also electrically separated from each other.

To realize such better stereoscopic visualization by an X-ray diagnostic apparatus, one proposal is disclosed, e.g., in the Japanese unexamined (Kokai) patent application No. 58-104593 (1983). This proposal is that the first and second X-ray sources and television cameras are arranged in relation to the object for the stereoscopic visualization, and when, for instance, the first X-ray source is energized, the first television camera can receive the image, but simultaneously the image incident upon the second television camera is interrupted. That is, the first and second X-ray sources and TV cameras are alternately operated to prevent the influences of the after-images by not mixing with each other the sequential images incident upon the same TV camera.

Other problems are revealed from the conventional X-ray diagnostic apparatus. Since two TV cameras are employed, two complex and expensive optical systems optically coupled between the X-ray sources and the two TV cameras are necessary which usually include the half mirrors, two TV lenses and the electronics shutters. However, as those optical elements cause a loss of light to a considerable degree, various measures must be taken, e.g., use of a lens having a small aperture value, or a small "F" value.

Moreover, the electrical characteristics of those TV cameras are inherently different from each other, so that an adjustment for the electrical characteristics of the resultant video signals takes a long time and makes difficult. Those electrical characteristics of the TV cameras are known as the gamma characteristics, the deflection size and distortion, and the input/output signal characteristics. As a result, those difficulties, on the other hand, cause an expensive X-ray diagnostic apparatus in cost and a bulky apparatus.

It is therefore an object of the present invention to avoid and overcome the above-described problems by employing a single television camera in an X-ray diagnostic apparatus having two X-ray radiation sources for the stereoscopic visualization.

SUMMARY OF THE INVENTION

The object may be realized by providing an X-ray diagnostic apparatus for allowing stereoscopic visualization on X-ray images of an object under examination, comprising:

means for irradiating and projecting intermittently X-rays toward the object at two different projection angles in relation to the object, thereby intermittently producing at least first and second X-ray transmission images;

first conversion means for converting the first and second X-ray transmission images into first and second electron images and finally into first and second visual images in synchronism with the X-ray projections, and for deviating center positions of the first and second visual images at its output focal plane by deflecting the first and second electron images; and second conversion means having at least first and second conversion regions and converting the first and second visual images intermittently incident upon the first and second conversion regions respectively into first and second video signals; and, means for controlling the X-ray irradiation and projection means, the first conversion means and the second conversion means in such a manner that the first and second X-ray transmission images are alternately produced, converted and deviated at the output focal plane, and when the first visual image is incident upon the first conversion region, electrical scanning of the first conversion region is blanked out for an optical storage of the first visual image therein, and also that of the second conversion region is performed during one scanning period upon which the second visual image has been previously incident.

Furthermore, an X-ray diagnostic apparatus for allowing stereoscopic visualization on X-ray images of an object under examination, comprises:

means for irradiating and projecting sequentially a plurality of X-rays toward the object at two different projection angles with respect to the object, thereby sequentially producing at least first, second, third and fourth X-ray transmission images respectively:

first conversion means for converting all of the X-ray transmission images into first, second, third and fourth electron images and finally into first, second, third and fourth visual images respectively in synchronism with the X-ray projections, and for deviating center positions between two relative visual images of the first, second, third and fourth visual images at its output focal plane by deflecting said two relative electron images;

second conversion means having at least first and second conversion regions and converting all of the visual images into first, second, third and fourth video signals;

means for injecting an X-ray contrast medium into a diagnostic portion of the object in synchronism with the X-ray projections in such a manner that at least the first and second X-ray video signals are obtained as mask image signals before the X-ray contrast medium is penetrated in the diagnostic portion, and at least the third and fourth X-ray video signals are obtained as contrast image signals after the X-ray contrast medium is penetrated therein;

means for digitally processing two relative video signals from the first, second, third and fourth video signals so as to derive at least a digital subtraction image signal, and means for performing controls of the X-ray irradiation and projection means, the first and second conversion means, the injection means, and the digital process means in such a manner that the first, second, third and fourth X-ray transmission images are sequentially produced in relation to the penetration of the X-ray contrast medium, converted and deviated at the output focal plane, when one of said two relative visual images is incident upon the first conversion region, electrical scanning of the first conversion region is blanked out for an optical storage of its visual image, and also that of the second conversion region is performed during one scanning period, upon which the remaining of said two relative visual images has been previously incident, whereby the digital subtraction is carried out between the two relative video signals.

BRIEF DESCRIPTION OF THE DRAWINGS

These and other objects and features of the invention will become apparent with reference to the following specification and to the drawings, in which.

DETAILED DESCRIPTION OF THE PREFERRED EMBODIMENTS

The basic idea of the present invention will now be described, before proceeding with preferred embodiments.

A plurality of X-rays are intermittently projected toward an object under examination at two projection angles with respect to an examination portion of the object for realizing the stereoscopic visualization. When the X-rays are interruptedly projected at two times, X-ray images having two different transmission data are intermittently and independently produced, which are like a right-viewed X-ray image and a left-viewed X-ray image respectively.

Those X-ray images are interruptedly incident upon an image converter, e.g., an X-ray image intensifier (referred to as an "image intensifier"), in which the incident X-ray images are converted into electron images, and then the electron images are converted into visual images in such a manner that the right-viewed visual image and the left-viewed visual image are alternately output at a predetermined deviation with respect to a center position of an output focal plane of the image converter by deflecting both the electron images by means of electrical deflection means, e.g., a deflection coil. Therefore, the right-viewed and left-viewed visual images are incident upon right and left regions of a target of a single television camera tube respectively and alternately. This single television camera scans those incident visual images in such a manner that when, for instance, the right-viewed visual image is incident upon the right region of the target, the scanning of the right target region is blanked out so as to optically store the right-viewed image therein and also the scanning of the left target region into which the left-viewed visual image has been previously and optically stored is performed during one TV scanning period, e.g., one field scanning period of 1/60 Hz so as to derive a video signal of the left-viewed visual image during the above-mentioned one TV scanning period.

In other words, the entire target region is divided into two regions, e.g., the right and left regions. The right-viewed visual image and the left-viewed visual image that are not simultaneously, but alternately output from the image converter, are alternately incident upon the corresponding right and left target regions respectively within one complete scanning period in synchronism with the X-ray projections. Accordingly those two target regions are alternately used for scanning and storing the right-viewed and left-viewed visual images during one complete scanning period. This one complete scanning period is defined by, e.g., one TV frame scanning period, or two TV field scanning fields of the interlaced scanning system.

Figure 1:
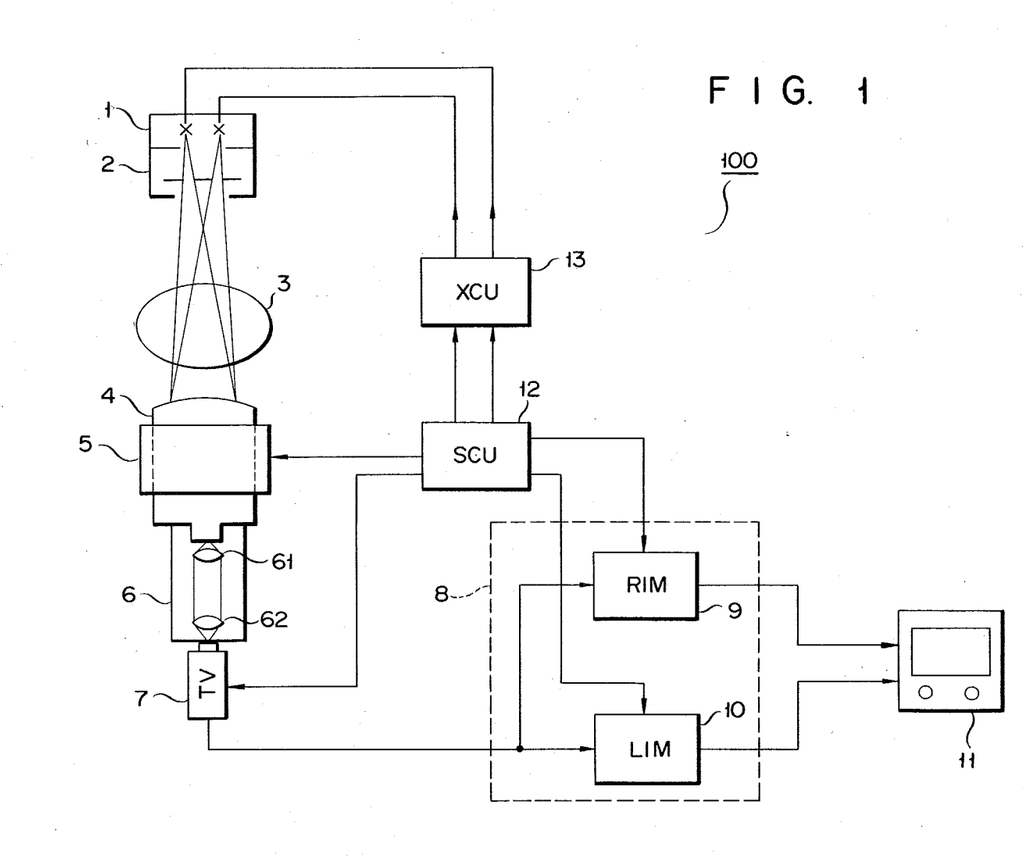
FIG. 1 is a block diagram of an X-ray diagnostic apparatus according to one preferred embodiment of the present invention.

Referring to FIG. 1, a stereoscopic X-ray diagnostic apparatus 100 according to one preferred embodiment will now be explained.

One target-two focal points stereoscopic X-ray tube 1 is provided. It has a truncated corn type rotary anode and two cathodes which are disposed to have a predetermined distance. Accordingly since thermions are emitted from the two cathodes and impinge on the two focal points of the target, the X-rays are irradiated therefrom at two different emission angles. An X-ray diaphragm 2 is provided with the X-ray tube 1 to limit the X-ray beam, whereby the X-ray which has passed through the diaphragm 2 can have a given beam shape. An object under examination 3, such as a patient is positioned to receive the X-rays irradiated from the X-ray tube 1. An image intensifier 4, as the above-described image converter, is arranged behind the object 3 along the X-ray travel path. The image intensifier 4 receives an X-ray transmission image converts it into an electron image and finally outputs a visual image from its output fluorescent plane. This image intensifier 4 may deviate center positions between two different visual images, i.e., the right-viewed and left-viewed visual images by supplying a deflection current to the build-in deflection coil 5. That is, when the input plane of the image intensifier 4 receives the left-viewed X-ray transmission image, the left-viewed visual image is derived from the output plane in such a manner that the center position of this image is deviated at the left side from a center position of the fluorescent output plane (will be described later).

An optical system 6 includes at least a primary lens 61 and a secondary lens 62 and is positioned in front of the output fluorescent plane so as to focus the visual images onto a single television (TV) camera 7. The TV camera 7 is therefore arranged to receive the visual images through the optical system 6 from the image intensifier 4. Precisely speaking, the right-viewed visual image is incident upon a right image conversion region (=target region) of the TV camera 7. The left-viewed visual image is incident upon a left image conversion region of the TV camera 7. The TV camera 7 is operated in synchronism with the X-ray projections as follows. When the left-viewed visual image is incident upon the left image conversion region of the TV camera 7, the electrical scanning, e.g., horizontal scanning for this region is blanked out so that a part of this visual image is opt-electrically stored therein, and also the electrical scanning for the right image conversion region is performed within one horizontal scanning field, into which the right-viewed visual image has been opt-electrically stored during last one TV field scanning period ($\approx 16.7$ mS). If the horizontal TV scanning system is employed, the first 32 $\mu S$ (approx. 64 $\mu S \times \frac{1}{2} \approx 32$ $\mu S$) scanning is stopped and the last 32 $\mu S$ scanning is effected (will be described later). That is, the scanning of one subdivided conversion region and the image storing of the remaining subdivided conversion region are alternately done during one TV horizontal scanning period. As a result, when the horizontal scanning is completed, i.e., one complete frame scanning period, the scanning of the right-viewed image and also that of the left-viewed image are accomplished so that both the right- and left-viewed video signals can be obtained within one frame scanning period. A digital image memory unit 8 is connected to the TV camera 7. The memory unit 8 is constructed by a right IC memory 9, a left IC memory 10, and an A/D converter (not shown). As the single TV camera 7 delivers alternately the right-viewed video signal and the left-viewed video signal, these video signals are separatedly stored in the right and left IC memories 9 and 10 respectively after being A/D-converted. A stereoscopic TV monitor 11 is connected to receive those video signals from the image memory unit 8. This TV monitor 11 employs the known polarized glasses system, or lenticulated sheet system, whereby the right-viewed and left-viewed visual images are simultaneously displayed on its screen (not shown in detail) for allowing the stereoscopic visualization based upon the above-described video signals that are read out from the digital IC memories 9 and 10.

A system control unit 12 is provided to control the entire system of the X-ray diagnostic apparatus 100. That is, this unit 12 produces the vertical sync signal for displaying the stereoscopic image on the screen of the TV monitor 11, X-ray trigger signals which are supplied to an X-ray control unit 13, the deflection current for the deflection coil 5 of the image intensifier 4, a beam blanking pulse in synchronism with the X-ray trigger signals and a storage trigger signal for designating the write-in operations of the image memory unit 8. The X-ray control unit 13 is under the control of the system control unit 12 in such a manner that when the X-ray trigger signals are supplied from the system control unit 12, either left-viewed X-ray or right-viewed X-ray is selectively irradiated from the stereoscopic X-ray tube 1. Consequently the stereoscopic visualization operation of the entire system can be achieved in synchronism with the projection timings of the X-rays under the control of the system control unit 12.

Now the operation of the stereoscopic X-ray diagnostic apparatus 100 will be described with reference to waveforms of FIG. 2.

As previously described, the system control unit 12 produces one X-ray trigger signal having, for example, 60 Hz for energizing the stereoscopic X-ray tube 1 in synchronism with the vertical sync signal at 60 HZ, and also the other X-ray trigger signal having the same frequency and function which is delayed by 1/60 second from the first-mentioned trigger signal. When both the X-ray trigger signals are in turn supplied to the X-ray control unit 13, a grid control voltage having, e.g., 3 to 5 (ms) duration time is applied to a control grid (not shown) of the X-ray tube 1, and then pulsatory X-rays each having several milliseconds' pulse width are alternately projected with the given time intervals at 60 pulses/sec. rate from the right and left focal points of the stereoscopic X-ray tube 1 respectively. In other words, the above duration time of the grid voltage can determine the duration time of the pulsatory X-ray.

The deflection current is supplied to the deflection coil 5 of the image intensifier 4 in synchronism with the right- and left-viewed X-ray projections, i.e., the right- and left-viewed X-ray trigger signals so that the right- and left-viewed electron images are deviated with respect to the center position of the output fluorescent plane of the image intensifier 4 by controlling the deflection current to the deflection coil 5. The beam blanking signal to stop the beam scanning for one half of the target region of the TV camera 7 is supplied to the camera 7 in synchronism with the X-ray trigger signals. The target region or the image conversion region is equally divided into two in this embodiment. The beam blanking signal and the beam scanning signal are supplied from the system control unit 12 to the TV camera 7. This control unit 12 controls the image storage unit 8 in synchronism with the X-ray trigger signals so that the right-viewed video signal and the left-viewed video signal are alternately stored in the right and left memories 9 and 10.

Referring to FIG. 2, assuming that the left-viewed X-ray projection is now carried out. Then the left-viewed X-ray transmission image incident on the image intensifier 4 is photoconductively converted and the converted visual image is also deviated by the deflection coil 5 from the center of the output fluorescent plane to the left side (see FIG. 2(A)). The deviation degree can be determined by the value of the deflection current flowing through the deflection coil 5. It is preferable to position the center "A" of the left-viewed visual image (=deviated visual image) apart from the center "O" of the non-deviated visual image, represented by a dot line, by approximately ⅔ radius of the latter image. When the left-viewed visual image is being derived from the output plane of the image intensifier 4, the beam scanning for the left target region of the TV camera 7 is blanked out (see FIG. 2(C)) and the beam scanning for the right target region thereof is performed within one even-numbered field (see FIG. 2(B)). In this case because the right-viewed X-ray transmission image is not incident upon the image intensifier 4, the right-viewed visual image does not appear. Accordingly no right-viewed video signal is output from the TV camera 7.

After 1/60 second from the above-described left view projection, a subsequent right-viewed X-ray projection commences. The right-viewed X-ray transmission image incident upon the image intensifier 4 is converted into the corresponding visual image and also this visual image is deviated from the center "O" to the right side (see FIG. 2(A) and even-numbered field image of FIG. 2(B)). Namely, a distance between the center "A" of the left-viewed visual image and the center "B" of the right-viewed visual image is about 4/3 radius of the non-deflected image. Preferably, a part of the input plane of the image intensifier 4 should be shielded by means of, e.g., a diaphragm so as to avoid the overlapping of each portion of both visual images. When the right-viewed visual image is output from the image intensifier 4 with a given deviation, the scanning of the right target region of the TV camera 7 is first blanked out, and subsequently only the left target region is electrically scanned during one even-numbered field. As a result, the left-viewed video signal is derived from the TV camera 7 and temporarily stored in the left memory 10. This left-viewed video signal is produced by the preceeding left-viewed X-ray projection. That is, when the right-viewed visual image appears at the output plane of the image intensifier 4, as the left-viewed visual image which has been already captured in the left target region during the preceding field is subsequently scanned, only the left-viewed video signal is derived and stored in the corresponding memory. Finally both video signals are read out from the memories 9 and 10 and stereoscopically displayed on the TV monitor 11. That is, both the left-and right-viewed images are simultaneously displayed on the TV monitor 11.

A detailed description will be made of the scanning system during both fields.

In the present embodiment, the raster scanning lines are selected to 525, and 1 (one) frame is constituted by 2 (two) fields. Further the normal interlaced scanning is employed. The left-viewed visual image is scanned during the even-numbered field, and the right-viewed one is done during the odd-numbered field. In other words, one full image, e.g., the left-viewed complete visual image can be completely scanned during one field period, i.e., a half frame period which is different from the standard TV scanning system.

Figure 2A:
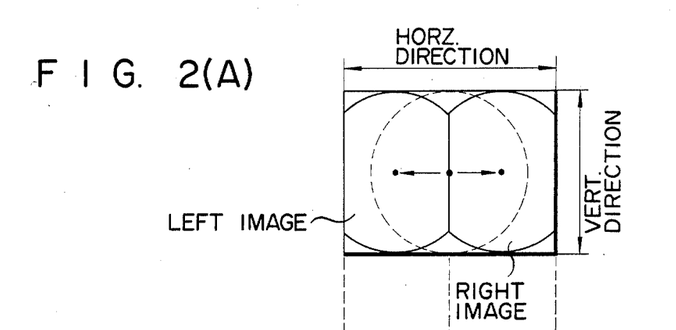
FIGS. 2A-2D show mainly waveforms of image signals of the apparatus in FIG. 1.
Figure 2B:
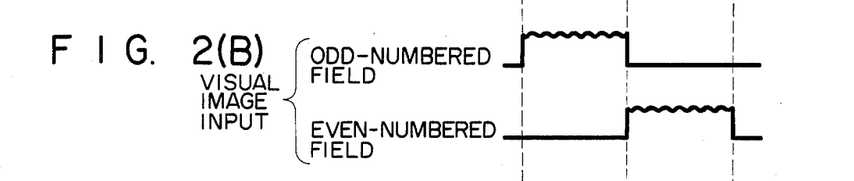
Figure 2C:
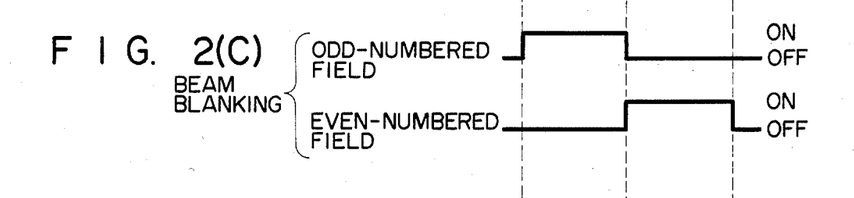
Figure 2D:
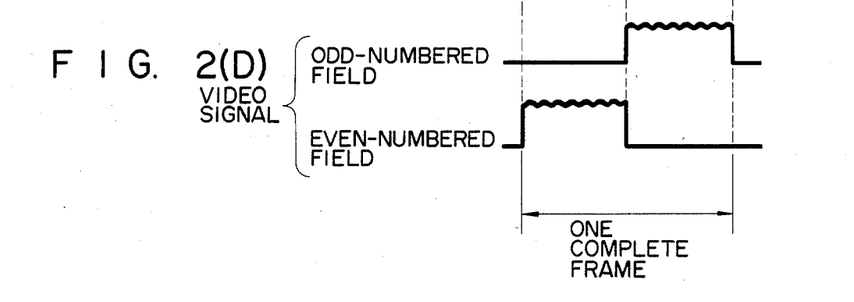

Then one horizontal scanning line of one field scanning period is taken into account. For example, the line scanning period for the left-viewed image of FIG. 2(A) is just a half of the horizontal scanning period (approximately $64 \ \mu S \times \frac{1}{2} \approx 32 \ \mu S$). The remaining half line period is for the right-viewed image. Therefore, the scanning of this remaining line period is blanked out. That is, one half of one horizontal scanning line is used to scan a part of one visual image and the other half is to blank out the beam scanning so as to optically store a part of the other visual image in the corresponding target region during one horizontal scanning line. This horizontal scanning is repeated at 525 times. Namely, for example, during the front half line period the left-viewed image is scanned and subsequently during the rear half line period the scanning is blanked out for optically store the right-viewed image. This one complete horizontal line scanning is repeatedly done at $525 \times \frac{1}{2}$ times (=even-numbered field period). During the odd-numbered field period, the front half line scanning is blanked out for a storage of the left-viewed image and the remaining half line scanning is effected for the right-viewed image.

As summarized above, the scannings of two different full images can be accomplished within one frame period. Accordingly, since the vertical scanning rate is selected to 60 Hz in the preferred embodiment, one complete image signal (left-or right-viewed video signal) can be obtained every 1/60 sec. Now the deterioration of the stereoscopic visualization will be considered. As previously described, at least 50 msec. time interval is required when the vidicon is employed. According to the present invention, there are provided two independent target regions in the TV camera tube, so that the right-viewed visual images and also the left-viewed visual images are independently incident upon their allocated target regions respectively. Therefore the after-image periods (50 msec.) occuring in the conversion of the right-viewed visual image are not necessarily overlapped with that of the left-viewed visual image. In other words, two different images, i.e., the right- and left-viewed images are not essentially mixed up with each other. As a result, the stereoscopic visualization is not deteriorated.

On the other hand, although the time interval among the images sequentially incident upon the same target region, e.g., the successive right-viewed images is shorter than the after-image period, i.e., approximately 16.7 msec. (1/60 sec), it can practically avoid the deterioration of the stereoscopic visualization because this time interval is sufficiently shorter than the after-image period of human's eyes, i.e., about 200 msec.

In accordance with the above-described embodiment, it is possible to shorten the X-ray projection interval and completely separate two different visual images by the deflection coil type image intensifier, so that better stereoscopic visualization can be achieved. Furthermore, since the single TV camera and thus the single optical system are employed, there is no loss in the light transfer. No electrical adjustment for the TV camera is required and thus the low cost stereoscopic X-ray diagnostic apparatus can be provided.

Another embodiment will now be described in accordance with the present invention. This embodiment relates to so-called "Digital Radiography" or "Digital Fluoroscopy" in which the time image subtraction and the digital image processing are utilized.

Before describing the second embodiment, the principle of the digital radiography, or digital fluoroscopy will be explained with reference to FIG. 3.

Figure 3:
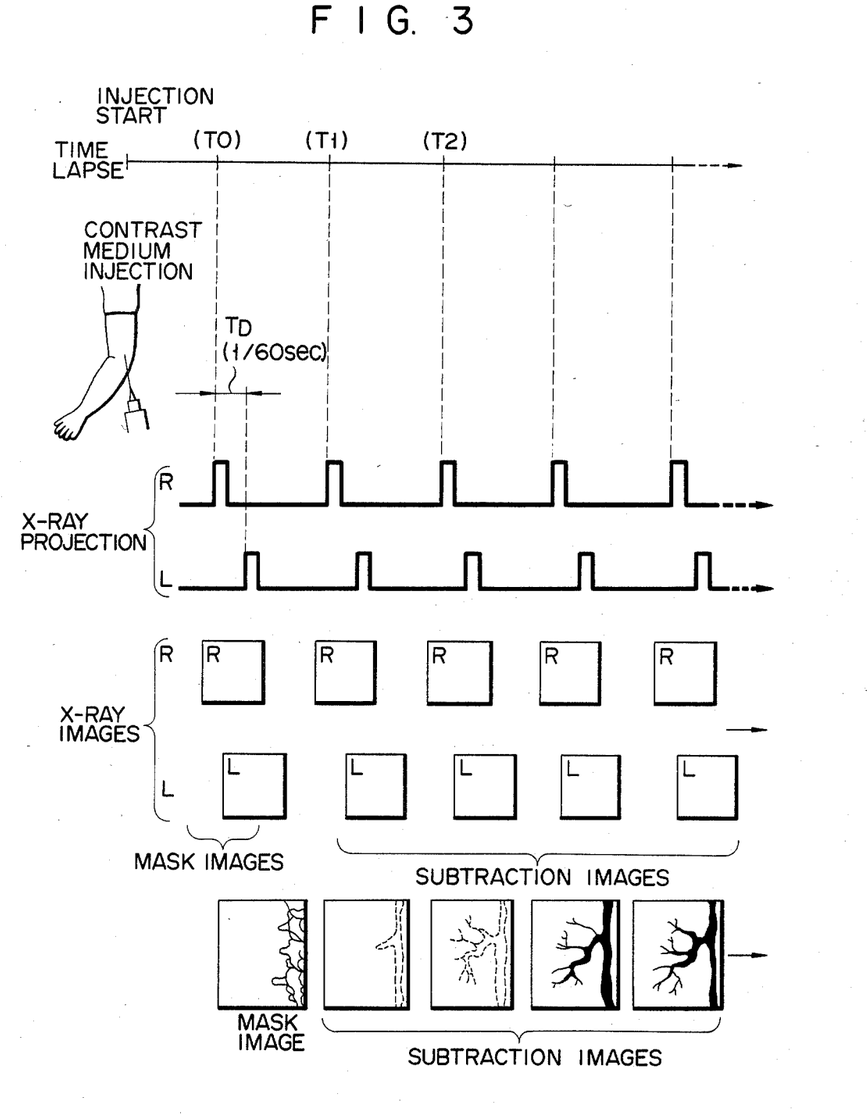
FIG. 3 shows an illustration for explaining the basic idea of the digital fluoroscopy.

As shown in FIG. 3, when time T0 has elapsed after an X-ray contrast medium for blood vessel is injected in an upper arm of an object to be examined such as a patient, a first X-ray projection is performed to photograph the portions of patient to be examined such as a heart by an X-ray TV camera (will be described later). X-ray television video signals from the X-ray TV camera are A/D converted, and the resultant digital X-ray television video signals to indicate mask images which contain no contrast medium are stored in a first digital memory (will be described later). When a time interval (T0+T1) has elapsed after the contrast medium had been injected, a second X-ray projection of the portion of the patient to be examined is performed. Thereafter, X-ray projections are intermittently performed at intervals of, for example one (1) second, and the diagnostic portion of the patient under examination is projected by X-ray beams and viewed by the X-ray TV camera while the contrast medium flows into the portion. X-ray television video signals are produced by the X-ray TV camera and are A/D converted into the digital X-ray television video signals which are stored in a second digital memory (will be described later). The X-ray television video signals which have been already stored in the first digital memory are subtracted from the X-ray television video signals which have been just stored in the second digital memory, thereby obtaining digital subtraction video signals of an angiogram or a subtraction image showning the penetration of contrast medium within blood vessels. The digital subtraction video signals are then D/A converted to obtained analogue subtraction video signals, so that subtraction images are displayed on a TV monitor.

Figure 4:
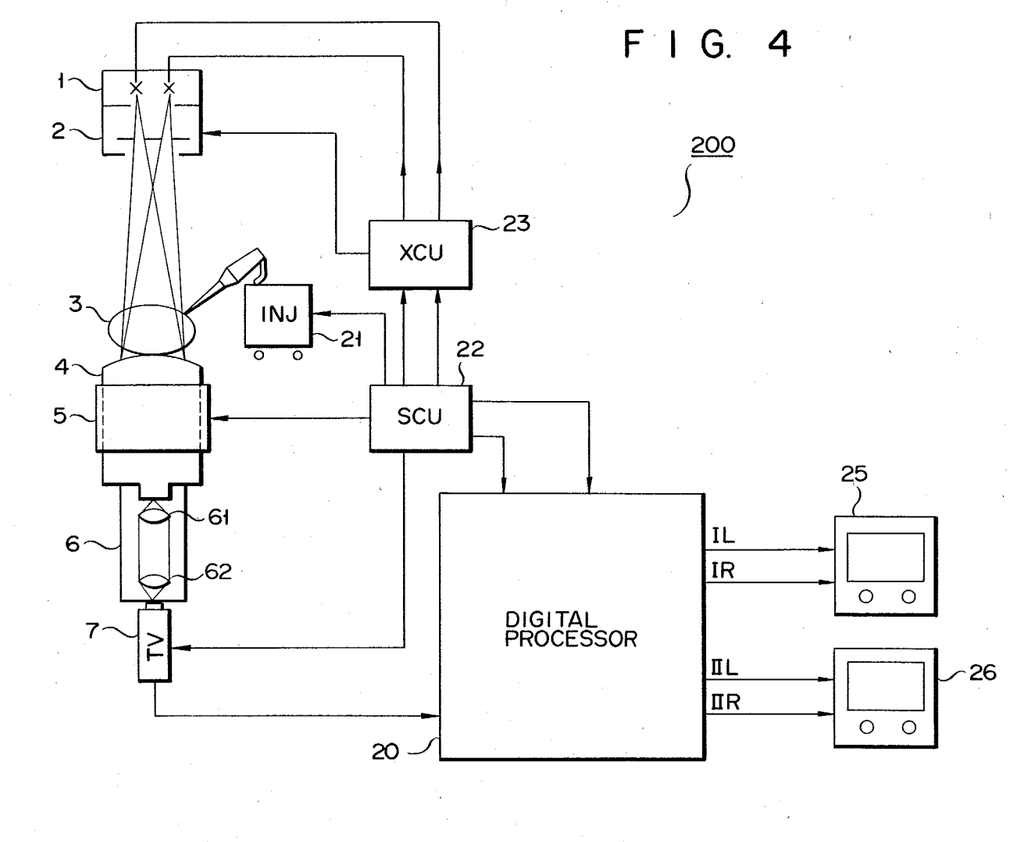
FIG. 4 is a block diagram of a digital fluoroscopy apparatus according to another preferred embodiment of the present invention.

Referring to FIG. 4, a stereoscopic digital fluoroscopy according to the present invention includes the same X-ray projection and image conversion system as in FIG. 1, a digital processor 20, an injector for X-ray contrast medium 21, a system control unit 22, an X-ray control unit 23 and two sets of TV monitors 25 and 26. Since the same X-ray projection and image conversion system are employed in this embodiment, a description of the operations and functions thereof is omitted.

The digital processor 20 separates from the TV signals derived from the TV camera 7 the right-viewed and the left-viewed image signals, converts those image signals into corresponding digital image signals, and performs the digital subtraction between the mask image signals and the contrast image signals, and also between the sequential contrast image signals by using the digital memories (will be described in detail).

The stereoscopic TV monitors 25 and 26 mainly allow to display stereoscopically the right-viewed and left-viewed mask images and subtraction images respectively by means of the known stereoscopic tools.

The system control unit 22 performs a control of the entire system, especially the administration of the X-ray contrast medium through the injector 21 in synchronism with the X-ray projection.

The X-ray control unit 23 controls the stereoscopic X-ray tube 1 and also the diaphragm 2 in such a manner that the visual image output from the image intensifier 4 can have a given contour in accordance with the normal digital fluoroscopy and the stereoscopic digital fluoroscopy.

Figure 5:
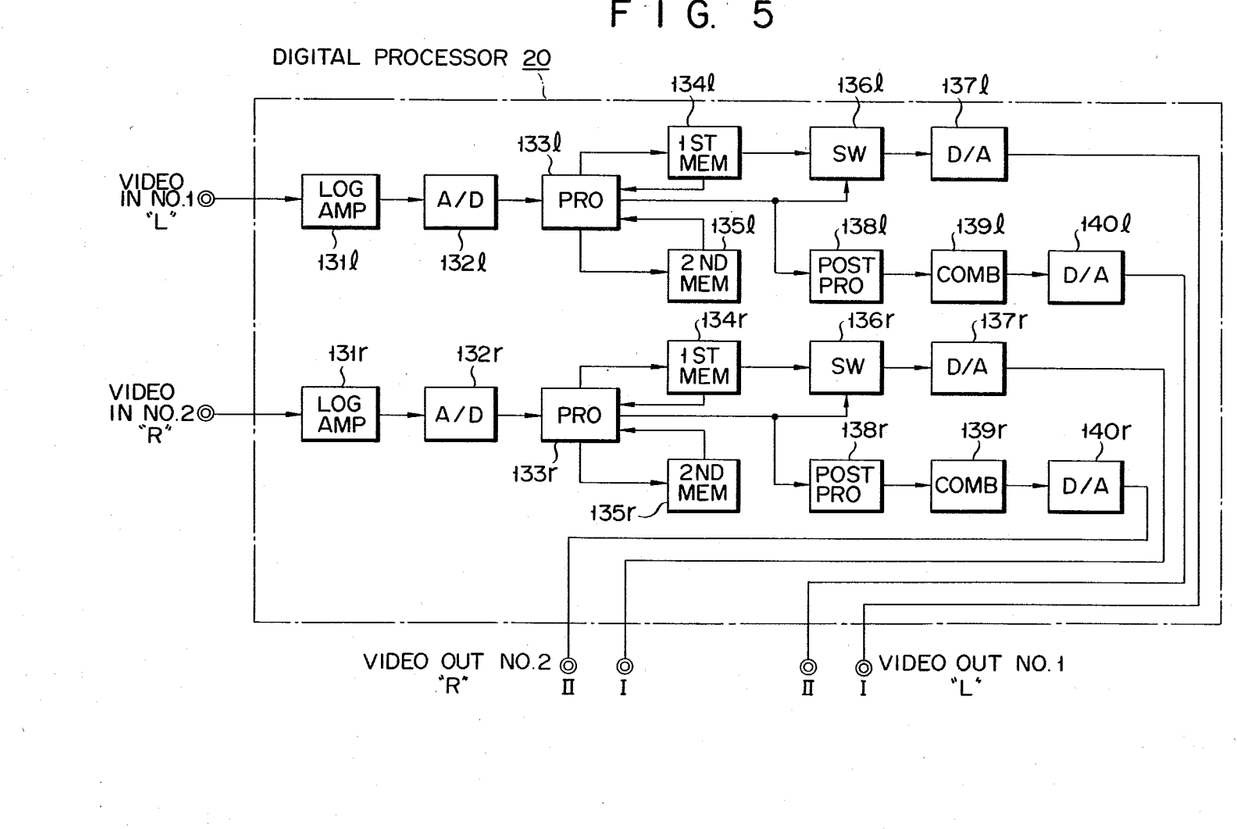
FIG. 5 is a block diagram of the internal circuit of the digital processor in FIG. 4.

FIG. 5 shows a block diagram of the internal circuit of the digital processor 20.

It should be noted that before the television signals derived from the TV camera 7 are supplied to this digital processor 20, the right-viewed TV signal which are contained in the above-mentioned television signals are separated from each other by the known separation method, e.g., the gating pulses. Further, although the system control signals which are supplied from the system control unit 22 are applied to the digital processor 20, those signals are omitted for a clear illustration.

The digital processor 20 shown in FIG. 5 will be described more in detail.

The digital processor 20 functions as an image processing unit which is a center of digital radiography.

Referring to FIG. 5, the digital processor 20 has one section for the right-viewed image which is suffixed by "r" and the other section for the left-viewed image which is suffixed by "l". Since these sections have the same arrangement, only one of these sections is described, whereas the other is only illustrated for the sake of simplicity. Furthermore, the arrangement for producing the right-viewed image is suffixed by "r" and the arrangement for producing the left-viewed image is suffixed by "l" as previously described. However, such suffixes are omitted in the following description.

Referring to FIG. 5, reference numeral 131 denotes a logarithmic amplifier (log amp); 132, an A/D converter; and 133, a processor using a given algorithm for executing the digital subtraction processing of two input images. Reference numeral 134 denotes a first digital memory for storing mask images; 135, a second digital memory for sequentially storing subtraction images obtained by the digital subtraction processing executed between the mask image and subsequently obtained contrast images; 136, a switch for selecting one of the mask image and the subtraction image so as to display a selected image on the display; and 137, a D/A converter. Reference numeral 138 denotes a post processor for emphasizing the stored subtraction image; 139, an image combining circuit for combining the subtraction images which have been emphasized; and 140, a D/A converter for producing an analogue subtraction video signal. The digital processor having the above arrangement uses a subtraction processing system which is synchronized with the interrupted X-ray projections.

The digital processor 20 operates as follows. The X-ray television signal (the video signal which corresponds to the mask image) obtained before the contrast medium penetrates or is injected into the diagnostic portion of the object 3 under examination is converted by the logarithmic amplifier 131 and the A/D converter 132 to a digital video signal. This digital video signal of the mask image is then stored in the first digital memory 134. Subsequently, the X-ray television signal (the video signal which corresponds to the contrast image) obtained when the contrast medium is penetrating into the object 3 under examination is converted by the A/D converter 132 to a digital video signal. The mask image's digital video signal stored in the first memory 134 is subtracted in the processor 133 from the contrast images digital video signal stored in the second memory 135 to obtain a digital subtraction image in accordance with the "Mask Mode Fluoroscopy". A resultant digital subtraction image is again stored in the second digital memory 135. In response to the switching operation of the switch 136, the digital video signal corresponding to the mask image is read out from the first digital memory 134 and supplied together with the subtraction image signal to the TV monitors 25, 26 after being converted into the analogue video signal in the D/A converter 137.

Figure 6:
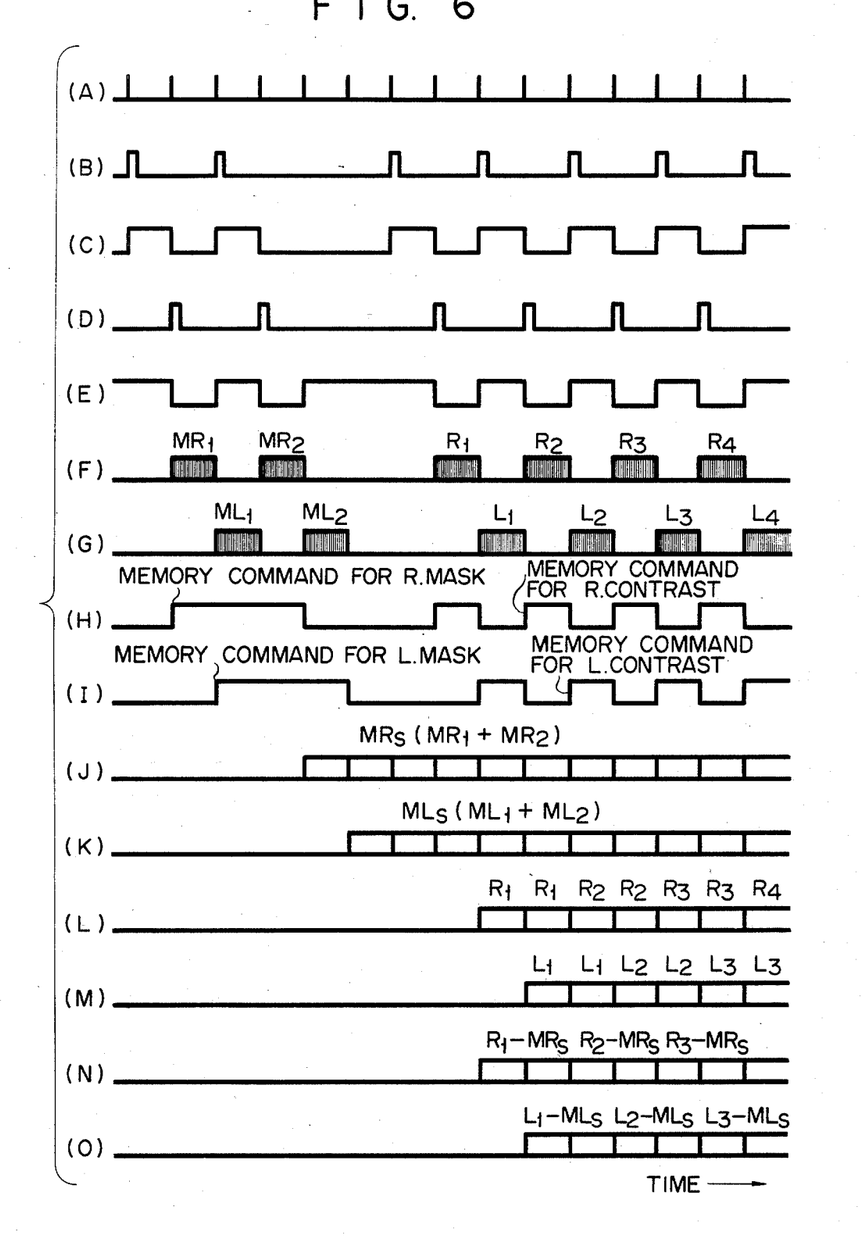
FIG. 6 shows a timing chart for explaining operations of the apparatus shown in FIG. 4.

Now the overall operation of the above-mentioned digital fluoroscopy apparatus 200 will be explained more in detail referring to a timing chart shown in FIG. 6.

The patient 3 is laid on a couch (not shown) for X-ray projection. The X-ray projection program which includes the X-ray projection conditions, delay times, X-ray projection intervals (images/second), total time of X-ray projections in seconds and the like is preset on a console deck (not shown). When the system control circuit 22 is set up, the operator depresses a start button (not shown) on the console deck. As shown in FIG. 3, when the time "t0" has elapsed after the contrast medium is automatically injected by the X-ray contrast medium injection device 21 into the patient 3 to be examined, the X-rays are interruptedly or intermittently irradiated from the X-ray tube 1.

The right cathode (not shown in detail) and then the left cathode (not shown in detail) of the X-ray tube 1 are alternately and sequentially operated under the control of the X-ray control unit 23. The thermion beams are alternately emitted from the right and left cathodes in such that first the right cathode and second the left cathode are intermittently operated with a delay time interval TD, e.g., 1/60 sec. (see FIG. 3), thereby projecting the right and left-viewed X-ray beams from the X-ray tube 1 alternately toward the patient 3. The X-ray projection is carried out in synchronism with the vertical sync pulse (see FIG. 6A).

The right-viewed X-ray image obtained by the first right X-ray projection (FIG. 6B) is converted to the visual image by the image intensifier 4. This visual image after being deviated by the deflection current (FIG. 6C) is converted to the right-viewed video signal by the TV camera 7 through the optical system 6. The right-viewed video signals MR1, MR2 (FIG. 6F) which are interruptedly produced in synchronism with the X-ray projections are A/D-converted in the digital processor 20. The digital right-viewed video signals are superimposed by each other and then stored as the mask image signal MRs (FIG. 6J) in the first digital memory 134r under the control of memory command for the right-viewed image (FIG. 6H). Likewise, the left-viewed X-ray image ML1, ML2 (FIG. 6G) obtained by the first left X-ray projection (FIG. 6D) can be stored as the digital mask image signal MLs (FIG. 6K) in first digital memory 135l of the digital processor 20 through the same TV camera 7 under the control of memory command for the left-viewed image (FIG. 6I). As a result, the mask image signals MRs, MLs (FIGS. 6J and 6K) are obtained by the first right- and left-viewed X-ray projection, as previously explained.

After acquisition of the video mask image signals MR1, MR2, ML1, ML2 is accomplished, the X-ray contrast medium is penetrating through the diagnostic portion of the object, which has been administered by the injector 21 under the control of the X-ray control unit 23 in synchronism with the X-ray projection. For the sake of the noise reduction in the acquired mask images, the first mask image video signals MR1, ML1 are summed by the second mask image video signals MR2, ML2 in the algorithmic processors 133r, 133l respectively (FIGS. 6J and 6K).

Fifth and sequential X-ray projections are performed for right-and left-viewed contrast images after the administered X-ray contrast medium arrives at the diagnostic portion. In the similar manner to the mask image processing, the digital video signals are sequentially obtained in the algorithmic processors 133r and 133l for the contrast image signals (FIG. 6F and 6G). Those digital video signals which indicate the different penetration conditions, or concentrations of the X-ray contrast medium in the diagnostic portion are then sequentially stored in the second digital memories 134r and 134l of the digital processor 20. The mask image's digital video signal read out from the first memory 134 is then subtracted from the contrast image's digital video signal which has been just stored in the second memory 135 by the algorithmic processor 133, thus obtaining a digital subtraction image (FIGS. 6N and 6O). That is, the digital subtraction is carried out between the two relative video signals. Upon switching operation of the switching circuit 136, the analogue video signals of the right- and left-viewed mask images (FIGS. 6J and 6K) and the analogue video signals for the right-and left-viewed subtraction images (FIGS. 6N and 6O) are delivered from the video processor 20 to the video out terminals. Those video signals are supplied to the TV monitors 25, 26, so that the right-viewed and left-viewed mask images are simultaneously displayed on the TV monitor 25, and the right-viewed and left-viewed subtraction images are simultaneously and sequentially displayed on the TV monitor 26.

According to another embodiment, a plurality of X-rays are alternately and sequentially projected from two different X-ray sources every 1 field (1/60 sec.), and the duration time of the X-ray is shortly selected to 2/1000 second. The sequential visual images are deviated from each other, so that no image mixture occurs. The left-viewed and right-viewed video signals are sequentially derived as the mask image signal and the contrast image signal without the influence of the after-image in connection with the administration of the X-ray contrast medium. Accordingly, such a diagnostic portion as the coronary arteries which moves at higher speed than other portion can be stereoscopically observed in the stereoscopic subtraction images. Moreover since the digital memories are employed to store the resultant video signals, the projection times of the X-rays can be reduced, with result that the patient is not suffered from the excessive X-ray projection.

While the invention has been described in terms of certain preferred embodiments, and exemplified with respect thereto, those of skill in the art will readily appreciate that various modification, changes, omissions, and substitutions may be made without departing from the spirit of the invention.

It is also possible to employ two TV monitors in the first embodiment, and one TV monitor is independently used for one image. Consequently if this idea is introduced in the second embodiment, four TV monitors can be also utilized for stereoscopic visualization.

Further since the scanning speed can be freely varied, the stereoscopic visualization for the more rapidly-changed diagnostic portion than in the above embodiments can be realized if the field scanning period is selected to be, for example, 1/120 second.

What is claimed is:

1. An X-ray diagnostic apparatus for allowing stereoscopic visualization on X-ray images of an object under examination, comprising:

means for irradiating and projecting intermittently X-rays toward the object at two different projection angles in relation to the object, thereby intermittently producing at least first snd second X-ray transmission images;

first conversion means for converting the first and second X-ray transmission images into first and second electron images and finally into first and second visual images in synchronism with the X-ray projections, and for deviating center positions of the first and second visual images at its output focal plane by deflecting the first and second electron images;

second conversion means having at least first and second conversion regions and converting the first and second visual images intermittently incident upon the first and second conversion regions respectively into first and second video signals; and, means for controlling the X-ray irradiating and projecting means, the first conversion means and the second conversion means in such a manner that the first and second X-ray transmission images are alternately produced, converted and deviated at the output focal plane, and when the first visual image is incident upon the first conversion region, electrical scanning of the first conversion region is blanked out for an optical storage of the first visual image therein, and also electrical scanning of the second conversion region, upon which the second visual image has been previously incident, is performed.

2. An apparatus as claimed in claim 1, further comprising:

means for temporarily storing the first and second video signals independently that are alternately derived from the second conversion means; and means for simultaneously displaying the first and second visual images of the object by processing the first and second video signals read out from the storing means.

3. An apparatus as claimed in claim 2, further comprising:

means having at least first snd second lenses and optically coupling the first conversion means to the second conversion means in such a manner that the first and second visual images alternately derived from the output focal plane of the first conversion means at a given deviation with respect to their center positions, are transferred through the first and second lenses and focused on the first and second conversion regions of the second conversion means respectively.

4. An apparatus as claimed in claim 2, further comprising:

an X-ray diaphram for limiting beams of the X-rays irradiated from the X-ray irradiating and projecting means.

5. An apparatus as claimed in claim 2, wherein the first conversion means is a deflection coil type X-ray image intensifier, the second conversion means is a single television camera, and the storing means is constructed of first and second digital memories.

6. An X-ray diagnostic apparatus for allowing stereoscopic visualization on X-ray images of an object under examination, comprising:

means for irradiating and projecting sequentially X-rays toward the object at two different projection angles with respect to the object to sequentially produce at least first, second, third and fourth X-ray transmission images respectively;

first conversion means for converting all of the X-ray transmission images into first, second, third and fourth electron images and finally into first, second, third and fourth visual images respectively in synchronism with the X-ray projections, and for deviating center positions between two relative visual images of the first, second, third and fourth visual images at its output focal plane by deflecting two relative electron images;

second conversion means having at least first and second conversion regions and converting all of the visual images into first, second, third and fourth video signals;

means for injecting an X-ray contrast medium into a diagnostic portion of the object in synchronism with the X-ray projections in such a manner that at least the first and second X-ray video signals are obtained as mask image signals before the X-ray contrast medium is penetrated in the diagnostic portion and at least the third and fourth X-ray video signals are obtained as contrast image signals after the X-ray contrast medium is penetrated therein;

means for digitally processing two relative video signals from the first, second, third and fourth video signals so as to derive at least a digital subtraction image signal; and means for controlling the X-ray irradiating and projecting means, the first and second conversion means, the injecting means, and the menas for digitally processing in such a manner that the first, second, third and fourth X-ray transmission images are sequentially produced in relation to the penetration of the X-ray contrast medium, converted and deviated at the output focal plane, when one of said two relative visual images is incident upon the first conversion region, electrical scanning of the first conversion region is blanked out for an optical storage of its visual image, and also electrical scanning of the second conversion region, upon which the remaining of said two relative visual images has been previously incident, is performed, said means for performing, carrying out digital subtraction of the two relative video signals.

7. An apparatus as claimed in claim 6, wherein the means for digitally processing includes:

first and second A/D converters for converting the two relative video signals from the second conversion means into two relative digital video signals respectively:

first and second algorithmic processors for performing at least the digital subtraction between the two relative digital video signals so as to derive the digital subtraction image signal;

first and second digital memories for temporarily storing the two relative video signals and also the corresponding digital subtraction image signal which are obtained from the first algorithmic processor;

third and fourth digital memories for temporarily storing the two relative video signals and also the corresponding digital subtraction image signal which are obtained from the second algorithmic processor; and first and second D/A converters for converting the two relative video signals and the corresponding digital subtraction image signals into analogue video signals and image signals, which are derived from the first and second algorithmic processors respectively.

8. An apparatus as claimed in claim 6, further comprising:

first means for simultaneously displaying the two subtraction image signals derived from the first and second algorithmic processors, said subtraction image signals being obtained before the X-ray contrast medium is penetrated into the diagnostic portion of the object; and second means for simultaneously displaying the two subtraction image signals derived from the first and second algorithmic processors, said subtraction image signals being obtained after the X-ray contrast medium is penetrated into the diagnostic portion of the object.

9. An apparatus as claimed in claim 6, further comprising:

means having at least first and second lenses and optically coupling the first conversion means to the second conversion means in such a manner that the two relative visual images alternately derived from the output focal plane of the first conversion means at a given deviation with respect to their center positions, are transferred through the first and second lenses and focussed on the first and second conversion regions of the second conversion means respectively.

10. An apparatus as claimed in claim 6, further comprising:

X-ray diaphragm means for limiting beams of the X-rays irradiated from the X-ray irradiating and projecting means.

11. An apparatus as claimed in claim 6, wherein the first conversion means is a deflection coil type X-ray image intensifier; and the second conversion means is a single television camera.

* * * * *